United States Patent [19]

George et al.

[11] Patent Number: 5,034,134
[45] Date of Patent: Jul. 23, 1991

[54] TREATMENT OF IMPURITY-CONTAINING LIQUID STREAMS IN ETHYLENE OXIDE/GLYCOL PROCESSES WITH SEMI-PERMEABLE MEMBRANES

[75] Inventors: Kathleen F. George, Cross Lanes; Lise Dahuron; John H. Robson, both of Charleston; George E. Keller, II, South Charleston, all of W. Va.

[73] Assignee: Union Carbide Chemicals And Plastics Technology Corporation, Danbury, Conn.

[21] Appl. No.: 457,923

[22] Filed: Dec. 27, 1989

[51] Int. Cl.$^5$ .............................................. B01D 61/00
[52] U.S. Cl. .................................... 210/651; 210/654
[58] Field of Search ............... 210/634, 644, 649–655, 210/500.1, 500.21, 500.27–500.32, 500.36, 500.41

[56] References Cited

U.S. PATENT DOCUMENTS

| | | |
|---|---|---|
| 3,904,656 | 9/1975 | Broz . |
| 4,277,344 | 7/1981 | Cadotte . |
| 4,427,507 | 1/1984 | van Aken et al. . |
| 4,737,325 | 4/1988 | Kamiyama et al. . |
| 4,830,712 | 5/1989 | Crandall et al. . |
| 4,830,885 | 3/1989 | Tran et al. . |

FOREIGN PATENT DOCUMENTS

1463324 2/1977 European Pat. Off. .

Primary Examiner—Frank Sever
Attorney, Agent, or Firm—Sharon H. Hegedus

[57] ABSTRACT

A method is disclosed for separating impurity components, UV absorbers and/or UV absorber precursors contained in an ethylene glycol-water stream thereby desirably allowing the recovery of the glycols contained in such stream in an economical and efficient manner. Specifically, these undesirable components are separated by contacting the ethylene glycol-water stream with a suitable semi-permeable membrane to effect such separation.

77 Claims, 1 Drawing Sheet

TREATMENT OF IMPURITY-CONTAINING LIQUID STREAMS IN ETHYLENE OXIDE/GLYCOL PROCESSES WITH SEMI-PERMEABLE MEMBRANES

BACKGROUND OF THE INVENTION

1. Field Of The Invention

This invention pertains to the field of separating particular constituents dissolved in a liquid medium by the use of semi-permeable membranes. More specifically, the present invention relates to the separation of ethylene glycols from at least one aliphatic organic acid having one or more carbon atoms or an alkali metal or alkaline earth metal salt thereof, at least one ultraviolet-light absorber or its precursor, or combinations thereof. The invention is particularly useful in the process for making polyester-grade monoethylene glycol from ethylene oxide.

2. Discussion Of Related Art

The preparation of ethylene glycol is of particular interest to the chemical industry because of the varied uses of this compound. A particularly important use of ethylene glycol is in the production of polyester fibers. Ethylene glycol used in the manufacture of polyester fibers generally must be of exceptionally high purity because even a small quantity of impurity may have a deleterious effect on the resulting polyester fiber. Ethylene glycol also finds application in heat-transfer fluids, deicing fluids, antifreeze, hydraulic fluids, and in the manufacture of alkyd resins and solvents.

The ability to increase the purity of ethylene glycol product is of particular interest for the manufacture of polyester fiber. When ethylene glycol contains even small quantities of impurities, the properties of the polyester produced, such as fiber dyeing characteristics, fiber strength, fiber color, etc., generally are affected adversely. High purity ethylene glycol suitable for use in the product of polyester fiber is referred to as polyester-grade ethylene glycol.

In order for ethylene glycol to qualify as polyester-grade ethylene glycol, it must pass a stringent ultraviolet light (UV) transmittance test. This test is conducted by comparing the transmittance of ultraviolet light at designated wavelengths through samples of ethylene glycol and of distilled water. The amount of ultraviolet light transmitted through a sample of distilled water of similar thickness, converted to a percentage, constitutes the percent transmittance of an ethylene glycol sample. Current commercial fiber-grade ethylene glycol ultraviolet light transmittance specifications are set forth below:

| Ultraviolet Light | |
|---|---|
| Wavelength (nanometers) | Minimum Percent Transmittance (%) |
| 220 | 70 |
| 275 | 90 |
| 350 | 98 |

As used herein, the term "UV absorbers" refers to materials which, when present in a sample of ethylene glycol, undesirably reduce the transmittance of ultraviolet light through the sample. The term is also meant to include materials which are UV absorber precursors, that is, materials which by themselves do not reduce the transmittance of ultraviolet light but which, when present during the preparation of the monoethylene glycol, are transformed to such UV absorbers. The reduction in the UV transmittance of an ethylene glycol sample is therefore a measure of the purity of that sample. In other words, the greater the UV transmittance of an ethylene glycol sample, the purer it is and the more valuable it becomes. Accordingly, it is preferable that the ethylene glycol not only satisfy the UV transmittance standards identified above, but that its UV transmittance be as high as possible.

Ethylene glycols (monoethylene glycol, diethylene glycol, triethylene glycol and tetraethylene glycol) are prepared commercially by several methods well known to those skilled in the art. One of these methods involves a two-stage reaction system, the first stage of which requires the direct oxidation of ethylene with air or elemental oxygen over a suitable catalyst, typically a silver-containing catalyst, at elevated temperature (100° C. to 500° C. is typical) and at superatmospheric pressure (2 to 25 atmospheres).

Ethylene oxide produced in these reactors, which may be fixed or fluid bed reactors, as typified by U.S. Pat. Nos. 2,125,333, 2,430,443, 3,904,656 and 3,970,711, is removed from the reactors in a gas stream and is passed into an ethylene oxide scrubber where the gas stream is contacted with water to absorb the ethylene oxide content thereof. The gases leaving the scrubber as overhead (which still contain appreciable quantities of ethylene) are then recycled to the ethylene oxide reactor. The scrubber bottoms, i.e., the ethylene oxide containing water is then passed to a stripper. In the stripper, steam or hot water may be introduced and contacted, usually countercurrently, with the ethylene oxide fed to the column to remove ethylene oxide product overhead. Alternatively, the ethylene oxide containing water may be subjected to temperature and pressure conditions within the stripper which remove the ethylene oxide as overhead. The water discharged from the stripper as bottoms is generally recirculated to the scrubber for reuse in absorbing ethylene oxide.

Inasmuch as water is constantly being generated in the ethylene oxide reactor at the same time as the aqueous stripper bottoms are being recycled to the scrubber in a closed system, a purge stream is required to remove the excess water which accumulates. This purge stream, however, generally contains appreciable quantities of ethylene glycols, typically up to about 10 percent by weight. Most of the contained glycols consist of monoethylene glycol (about 0.1 to about 10.0% by weight) with the remainder being diethylene glycol (about 0.01 to about 1.0% by weight), triethylene glycol (about 0.001 to about 0.1% by weight), and trace levels of higher molecular weight glycols. As used herein, the term "ethylene glycols" is meant to include mono-, di-, and triethylene glycols as well as higher molecular weight glycols. The amount of glycols in this purge stream is of such value that it is not economically preferable to simply discard it. Hence, it may be introduced to a glycol reactor in which ethylene oxide and water are reacted to form ethylene glycols or into the refining train downstream of the glycol reactor. The ethylene glycols produced in the glycol reactor are first passed to an evaporator wherein water is removed. The glycols product is taken from the evaporator as bottoms, and then passed through a distillation train to produce refined monoethylene glycol, the desired product, as well as diethylene glycol, triethylene glycol, tetraethylene glycol, etc. as by-products.

Frequently, however, the purge stream which contains the valuable glycols and which is introduced into the glycol process, may contain various impurities such as aliphatic organic acids having one or more carbon atoms and/or the alkali metal or alkaline earth metal salts thereof. Some of these acids and/or salts may comprise UV absorbers or their precursors. The purge stream may also contain one or more high molecular weight derivatives of ethylene oxide other than glycols which may also be UV absorbers or precurors which form UV absorbers during subsequent processing steps. Consequently, these impurities are deleterious to the monoethylene glycol product that is intended to be produced, preventing it from being classifiable as polyester-grade.

A need accordingly exists for providing a technique in which undesirable UV absorbers and/or their precursors which are contained in glycol-containing purge streams, such as the purge stream from the aqueous bottoms of the stripper, are economically and efficiently separated from the valuable glycols.

SUMMARY OF THE INVENTION

By virtue of the present invention, a new technique has been discovered which is capable of effectively separating the undesirable UV absorbers and/or their precursors contained in the purge stream of the bottoms recycle stream of the stripper column in an economical and efficient manner.

More particularly, these UV absorber and/or precursor components may be separated by contacting such a purge stream under pressure with a suitable semi-permeable membrane to effect such separation by reverse osmosis. Such a semi-permeable membrane may include an asymmetric membrane having a thin separation layer which determines the overall separation characteristics of the membrane. Alternatively, the semi-permeable membrane may also include a composite membrane comprised of a porous support layer having substantially no separation characteristics with respect to the UV absorber and/or their precursor components and a separation layer positioned on the support layer which substantially determines the selective permeation characteristics of the overall composite membrane.

Thus, the present invention, in one embodiment, is directed to a method for separating ethylene glycols from at least one impurity component comprising an aliphatic organic acid having one or more carbon atoms, an alkali metal or alkaline earth metal salt of such aliphatic organic acid, or a combination thereof; said glycols and said at least one impurity component being substantially dissolved in a liquid medium capable of acting as a solvent for said glycols and the at least one impurity, which comprises contacting the liquid medium containing the said glycols and at least one impurity with one surface of a semi-permeable membrane which exhibits selective permeation for the glycols over that of the at least one impurity, and removing from the vicinity of the opposite surface of the semi-permeable membrane a permeate having a concentration of the at least one impurity which is less than the concentration of the at least one impurity in the liquid medium.

In another embodiment, the present invention is directed to separating UV absorbers from ethylene glycols which are contained in a liquid medium. Specifically, this embodiment is a method of separating ethylene glycols from at least one UV absorber and/or UV absorber precursor; said glycols and said at least one UV absorber and/or UV absorber precursor being substantially dissolved in a liquid medium capable of acting as a solvent for said glycols and the at least one UV absorber and/or precursor, which comprises contacting the liquid medium containing the said glycols and at least one UV absorber and/or precursor with one surface of a semi-permeable membrane which exhibits selective permeation for the glycol over that of the at least one UV absorber and/or precursor, and removing from the opposite surface of the semi-permeable membrane a permeate having a concentration of the UV absorber and/or precursor which is less than the concentration of the UV absorber and/or precursor in the liquid medium.

In yet another embodiment, the present invention is directed to a process for the manufacture of ethylene oxide which includes the steps of:

a) reacting oxygen and ethylene in a reactor in the presence of a catalyst at ethylene oxide producing conditions to produce ethylene oxide;

b) absorbing ethylene oxide produced in step (a) in water in a scrubber to produce an ethylene oxide-water stream;

c) stripping ethylene oxide from the ethylene oxide-water stream produced in step (b) in a stripping column to produce an ethylene oxide overhead stream and an aqueous bottoms stream, said aqueous bottoms stream comprising water, UV absorbers and/or UV absorber precursors, and mono-, di-, tri- and/or higher molecular weight ethylene glycols;

d) recycling aqueous bottoms from the stripping column to the scrubber of step (b); wherein the improvement comprises removing as a purge stream a portion of the recycled aqueous bottoms from the stripping column of step (d) and treating at least a portion of said purge stream by contacting the purge stream containing the said glycol and at least one UV absorber and/or UV absorber precursor with one surface of a semi-permeable membrane which exhibits selective permeation for the glycol over that of the at least one UV absorber and/or UV absorber precursor, and removing from the vicinity of the opposite surface of the semi-permeable membrane a permeate having a concentration of the UV absorber and/or UV absorber precursor which is less than the concentration of the UV absorber and/or UV absorber precursor in the purge stream.

In preferred embodiments of the present invention, composite membranes are utilized to carry out the specified separation.

A particularly preferred composite membrane which provides excellent separation and permeation as well as excellent chemical stability and resistance to the components of the purge stream is a separation layer comprised of sulfonated-polysulfone and a support layer comprised of polysulfone.

DETAILED DESCRIPTION OF THE INVENTION

While the present invention is primarily directed to the field of ethylene oxide/ethylene glycol production, particularly the manufacture of polyester-grade ethylene glycol by the removal of impurity components, UV absorbers, and/or UV absorber precursors, it is understood that the invention is not limited exclusively to this technological field. Rather, the invention is directed to the separation of the impurity components, the UV absorber, and/or UV absorber precursor components which are typically found in such ethylene oxide/ethylene glycol production techniques but which may be present in other processing environments as well.

As noted earlier, the term "UV absorber", as used herein, is meant to include any material which may be present in a processing stream (such as the aqueous purge stream of the recycled bottoms from the stripper column) in the ethylene oxide production process which causes a reduction in the UV transmittance in an ethylene glycol sample containing such components. The term is also meant to include materials which are UV precursors, i.e., materials which undergo a transformation during processing and ultimately form UV absorbers which may be found in the monoethylene glycol product. These UV absorber components may include aliphatic organic acids having one or more carbon atoms or the alkali metal and/or alkaline earth metal salts of these aliphatic organic acids. These salts include, but are certainly not limited to, for example, sodium, potassium, magnesium, calcium, and the like, salts of formic acid, acetic acid, glycolic acid, oxalic acid and the like. While these acids and/or salts are generally all characterizable as being impurities in the ethylene oxide/glycol processes, they may not all be characterizable as being UV absorbers. Nevertheless, their removal from the monoethylene glycol product would obviously still be very much desirable.

Other UV absorbers and/or UV absorber precursors which may be present in the purge stream and which are capable of being separated by the processes of the present invention include ethylene oxide derivatives other than glycols having a molecular weight of at least about the molecular weight of monoethylene glycol. Such derivatives include, for example, but are not limited to, high molecular weight aldehydes, and the like. Moreover, the methods of the present invention are able to separate UV absorbers and their precursors which have not as yet even been fully identified or well defined. These unidentified UV absorbers and/or UV absorber precursors are present in the processing streams of the ethylene oxide/ethylene glycol processes in such limited and minute quantities, that their isolation and identification have been quite elusive. Yet, the presence of even such minute quantities of these still unidentified UV absorbers and/or their precursors have a significant effect on the reduction of the UV transmittance of the ethylene glycol sample prepared from a processing stream containing these impurities. However, although they may be unidentified, when subjected to reverse osmosis in accordance with the present invention using a suitable semi-permeable membrane, these unidentified UV absorbers/UV absorber precursors are nevertheless removed as noted by the substantial increase in UV transmittance of the ethylene glycol sample. Hence, the present invention includes within its scope the removal of any UV absorber and/or UV absorber precursor albeit unidentified.

By virtue of the present invention, it has been discovered that suitable semi-permeable membranes, particularly composite membranes, can effectively be utilized in a reverse osmosis manner to separate these UV absorber components and/or their precursors from the ethylene glycols (mono-, di-, tri-, tetraethylene glycol and higher molecular weight ethylene glycols) when these constituents are substantially dissolved in a liquid medium. Typically, the liquid medium is water but it is not limited to such a solvent. Of course, the semi-permeable membrane which is utilized for the separation must be such that it is not chemically degraded by the solvent in which these constituents are present or by the constituents themselves.

In the present invention, it has been discovered that when a liquid medium containing ethylene glycols and UV absorbers is contacted with a suitable semi-permeable membrane while being subjected to a suitable feed pressure, the ethylene glycols will permeate through the semi-permeable membrane at a rate which is substantially greater than that of the UV absorbers. This, in effect, rejects the undesirable impurities, such as the UV absorbers, from the purge stream and produces a substantially purified purge stream which when utilized in a glycol process is capable of producing polyester-grade ethylene glycol.

However, and most importantly, we have also discovered that there are membranes, particularly composite membranes, which not only have excellent separation and permeability characteristics but which are, additionally, chemically resistant to these components and the solvent in which they are present.

To achieve selective separation, the semi-permeable membrane must exhibit less resistance to the permeation of one or more components than that of at least one other component contained within the liquid medium as such liquid medium is being forced by applied pressure against the membrane. Thus, selective separation can provide preferential depletion or concentration of one or more desired components in the medium with respect to at least one other component and therefore provides a product having a different proportion of the one or more desired components to the at least one other component than that proportion in the liquid medium.

However, in order for membrane separation of one or more desired components to be commercially attractive, the membranes must not only be capable of withstanding the conditions to which they may be subjected during the separation operation, but also must provide an adequately selective separation of the one or more desired components, i.e., a high separation factor, as well as a sufficiently high flux, i.e., a high permeation rate, so that the use of such a separation procedure is carried out on an economically attractive basis.

With respect to the UV absorbers and the ethylene glycols, alteration of the chemical structure of the membrane may occur, particularly if a polymer-based membrane is utilized, if these constituents are contained in a liquid medium other than water. Such alteration may sometimes be acceptable if it does not lead to deterioration of long term membrane performance. Thus, the ethylene glycols and the impurities may be present in solvents such as, for example, alcohols, glycols, glycol ethers, glycol carbonates, combinations thereof, and the like, and would then require the use of membranes which are chemically resistant to such alternative solvents while still desirably providing good selectivity and flux.

By virtue of the present invention, as a preferred embodiment, it has been determined that composite membranes, particularly sulfonated polysulfone on polysulfone composite membranes, are capable of providing desirably high separation factors and high permeation rates with respect to the UV components and the ethylene glycols discussed above, including excellent chemical stability when these constituents are present in an aqueous medium.

Asymmetric type membranes are comprised essentially of a single permeable membrane material distinguished by the existence of two distinct morphological regions within the membrane structure. One region comprises a thin, relatively dense semi-permeable skin capable of selectively permeating one component of a fluid mixture. The other region comprises a less dense, porous, non-selective support region that serves to preclude the collapse of the thin skin region of the membrane under pressure.

Composite membranes generally comprise a thin layer or coating of a suitable membrane material superimposed on a porous substrate. This coating layer, also referred to herein as a separation layer, determines the separation characteristics of the composite structure, and is advantageously very thin so as to provide the desirably high permeablity referred to above. The substrate or support layer only serves to provide a support for the membrane layer positioned thereon and has substantially no separation characteristics with respect to the liquid medium being separated or concentrated.

These membranes may be fabricated in various shapes, such as (1) a flat sheet which may be supported in a typical plate and frame structure similar to a filter press; (2) a flat sheet rolled into spirals with spacing materials interleaved with the membrane and the assembly sealed to provide spiroidal channels permitting the passage of the feed on one side of the coiled membrane to the opposite side of the membrane; (3) as tubes lining the inner surface of a reinforced braid, the braid itself at times being a component in a larger tube; or (4) in the form of open-ended hollow fibers so organized and sealed into header plates so as to provide a separation of the flow over the external surfaces of the hollow fibers from any flow within the bores of the hollow fibers ensuing by virtue of passage of the liquid feed mixture across the membrane. Such hollow fiber construction is preferred in the process of the present invention.

The invention is further described herein, for convenience of description, with particular reference to hollow fiber composite membranes. It will be understood, however, that the scope of the present invention is not limited to the use of the membranes in the composite structure in the hollow fiber form.

The hollow fiber membranes typically used in the art have continuous channels for fluid flow extending between the exterior and interior surfaces. Frequently, the substrate pores have an average cross-sectional diameter less than about 20,000 Angstroms and in some hollow fibers the cross-sectional diameter is less than about 1,000 or 5,000 Angstroms. Advantageously, the walls of the hollow fibers are sufficiently thick that no special apparatus is required for their handling. Frequently, the hollow fibers may have outside diameters of about 20 to 1,000 microns, generally about 50 to 500 microns, and have walls of at least about 5 microns in thickness, generally about 50 to about 450 microns thick. The wall thickness in some hollow fibers may be up to about 200 or 300 microns. The coating may have a thickness ranging from about 0.01 to about 10 microns and preferably has a thickness of about 0.05 to about 2 microns.

In order to provide desirable fluxes through the hollow fibers, particularly using those hollow fibers having walls at least about 50 microns in thickness, the hollow fibers may have a substantial void volume. Voids are regions within the walls of the hollow fibers which are vacant of the material of the hollow fibers. Thus, when voids are present, the density of the hollow fiber is less than the density of the bulk material of the hollow fiber. Often, when voids are desired, the void volume of the hollow fibers is up to about 90, generally about 10 to 80, and sometimes about 20 or 30 to 70, percent based on the superficial volume, i.e., the volume contained within the gross dimensions, of the hollow fiber. The density of the hollow fiber can be essentially the same throughout its thickness, i.e., isotropic, or the hollow fiber can be characterized by having at least one relatively dense region within its thickness in barrier relationship to fluid flow through the wall of the hollow fiber, i.e., the hollow fiber is anisotropic. Generally, a relatively dense region of anisotropic hollow fibers is essentially at the exterior or interior of the hollow fiber, and preferably, the coating contacts this relatively dense region.

The material used for the hollow fiber may be a solid, natural or synthetic substance. The selection of the material for the hollow fiber may be based on the heat resistance and/or mechanical strength of the hollow fiber, as well as other factors dictated by the separation process of the present invention and the operating conditions to which it will be subjected. Most importantly, the materials used, whether it be the porous support layer or the coating layer must be chemically resistant to each of the components in the liquid medium, including the solvent in which these components are contained. The hollow fibers may be flexible or substantially rigid.

The hollow fibers may be comprised of an inorganic material, e.g., hollow glass, ceramic, sintered metal, or the like. In the case of polymers, both addition and condensation polymers which can be fabricated in any suitable manner to provide porous hollow fibers, are included. Generally organic, or organic polymers mixed with inorganic materials (e.g., fillers), are used to prepare the hollow fibers. Typical polymers can be substituted or unsubstituted polymers and may be selected from polysulfones, such as bisphenol A polysulfone (sold under the mark "Udel" by Amoco Performance Products, Inc.) or polyether sulfone (sold under the mark "Victrex" by Imperial Chemical Industries); polyacrylonitriles; polyethers; polyamides; polyimides; cellulosic derivatives; poly(arylene oxides) such as poly(phenylene oxide); polyether ketones; polysulfides; polymers from monomers having alph-olefinic unsaturation other than mentioned above such as poly(ethylene), poly(propylene), poly(butene-1), poly(4-methyl 1-pentene), polyvinyls, e.g., poly(vinyl chloride), poly(vinyl fluoride), poly(vinylidene chloride), poly(vinylidene fluoride), and the like.

Substrates prepared from polysulfone are particularly preferred.

The polysulfone or other hollow fiber substrates employed in the practice of particular embodiments of the present invention can be prepared in accordance with conventional techniques well known in the art. Hollow fibers are generally spun from a dope composition of the desired fiber polymer, quenched, washed and dried. As disclosed by Cabasso, et al. in "Composite Hollow Fiber Membranes", Journal Of Applied Polymer Science, Volume 23, 1509–1525 (1979), and in "Research and Development of NS-1 and Related Polysulfone Hollow Fibers for Reverse Osmosis Desalination of Seawater", Gulf South Research Institute, July 1985, distributed by National Technical Information Service, U.S. Department of Commerce Publication PB No. 248,666, polysulfone hollow fibers can be spun from a ternary solution of polysulfone, poly(vinyl pyrrolidone) and dimethylacetamide, with the total polymeric concentration in the solution desirably being 40 to 52 weight %, and the poly-sulfone/poly(vinyl pyrrolidone) ratio being 1.5:2.0. The well known tube-in-tube jet technique is disclosed as being suitable for the spinning procedure, with water at about 21° C. being the preferred outside quench medium for the fibers. The quench medium in the center of the fiber is frequently air. Quenching is typically followed by washing the fibers, for example, conveniently with hot water at about 50 to 60° C. Following such washing, the hollow fibers are dried prior to being coated with the separation film layer to form the desired composite membrane. For this purpose, the polysulfone hollow fibers are typically dried by passage through a hot air drying column for a suitable period of time.

Hollow fiber substrates are typically substantially porous and the extent of their surface and bulk porosity is controlled by dry/wet, wet, dry or melt extrusion techniques which are well known to those skilled in the semi-permeable membrane art. The porosity of the hollow fibers may be further modified by solvent annealing or high temperature annealing techniques.

The coating layer of the composite membrane is in the form of an essentially non-interrupted membrane in contact with the porous support layer.

The materials for the coating may include, but are not limited to, cellulose derivatives, such as cellulose acetate; interfacial polycondensation polymers, such as polyamides, for example, those that are described in U.S. Pat. Nos. 4,277,344 and 4,830,885, the contents of which are incorporated herein by reference, and the like.

Most preferably, a sulfonated polysulfone is utilized as the coating material for the composite membrane. Such sulfonated polysulfones are discussed in, for example, U.S. Pat. No. 3,709,841, U.S. Pat. No. 4,054,707, U.S. Pat. No. 4,207,182, European Patent Application No. 0,202,849, European Patent Application No. 0,165,077 and European Patent Application No. 0,202,841 all of which are incorporated herein by reference as if set out in full. Sulfonated-polysulfones are also discussed in the Journal of Applied Polymer Science, Volume 20, pages 1885–1903 (1976) in an article entitled Sulfonated Polysulfone by A. Noshay, et al., the contents of which is also incorporated herein by reference.

Sulfonated polyarylether sulfones and sulfonated polyetherether sulfones are both applicable for use as the coating materials in the membranes utilized in the present invention. Such sulfonated polysulfones and reverse osmosis and ultrafiltration membranes thereof are disclosed in U.S. Pat. Nos. 4,414,368; 4,508,852; 4,268,650; and 4,273,903, which are also incorporated herein by reference.

Methods of preparation of sulfonated polyether ketones and salts thereof can be found in an article by Xigao Jin, et al., British Polymer Journal, Vol. 17, pp. 4–10, (1985).

Preparation of asymmetric sulfonated polyether ketone reverse osmosis membranes from sulfonated polyether ketones is described in U.S. Pat. No. 4,714,725, incorporated herein by reference.

Polyarylether sulfone with at least one sulfonic acid group present on one of the aromatic rings is one of the more common sulfonated polysulfones which is applicable in the present invention. Such a polyarylether sulfone generally has the formula as follows:

Sulfonated bisphenol A polysulfone is Particularly preferred as the coating for the separation layer for the composite membrane.

As used herein, the term "sulfonic group" is meant to be an optionally salified ——$SO_3H$ group, for example the groups ——$SO_3^{31}$, $1/_nM^{n+}$ where M represents an $NH_4^+$ ion, an alkali metal ion, an alkaline earth metal ion, or a transition metal ion (of valency n).

The sulfonation of polysulfone can be carried out in accordance with the procedures described in, for example, U.S. Pat. No. 3,709,841. Suitable sulfonating reagents include chlorosulfonic acid ($ClSO_3H$) which is a preferred sulfonating agent. However, it is also possible to use, for example, sulfur trioxide and its addition products with Lewis bases containing oxygen as the electron donor atom; sulfuric acid and fuming sulfuric acid can also be used. The sulfonation reaction is generally carried out at $-50°$ to $+80°$ C., preferably at $-10°$ to $+35°$ C., in solution in a solvent for the polyarylether sulfone which is inert as regards the sulfonation reaction. Halogenated hydrocarbons, especially methylene chloride, 1,2-dichloro-ethane and 1,1,2,2-tetrachloro-ethane are suitable solvents.

The amount of sulfonating agent employed is generally such that the ratio of the number of sulfur atoms of the sulfonating agent to the number of sulfur atoms of the non-sulfonated polyaryl-ether-sulfone is from about 0.3 to about 6, and preferably from about 1.2 to 4. The exact number of sulfo groups which can be fixed to the non-sulfonated polyaryl-ether can of course be altered by adjusting the sulfonation conditions and, in particular, the temperature, the duration of the reaction, and the concentration of the reagents. The sulfonated polyaryl-ether-sulfone produced can be isolated in accordance with the method described in, for example, U.S. Pat. Nos. 3,709,841 or 3,875,096.

Other methods for the preparation and isolation of a sulfonated polysulfone, known in principle from the prior art, can be adopted, by analogy, to prepare such sulfonated polysulfones.

Sulfonated polyarylethersulfones with degrees of substitution between about 1.0 to about 2.5 meq/g of dry polymer that are soluble in solvents such as methoxyethanol, nitromethane, and alcohol/water mixtures are particularly useful for the preparation of the composite membranes capable of effectively separating UV absorbers from ethylene glycols.

The dried polysulfone hollow fiber is coated with the coating solution of the sulfonatedpolysulfone and is then dried. Such a coating and drying sequence may comprise the technique used and described in the Coplan, et al. patent, U.S. Pat. No. 4,467,001, which is incorporated herein by reference. Thus, the dried hollow fibers are passed through the coating solution contained in a coating vessel, and are then passed through a drier oven and a cure oven for contact with drying air or other suitable gas, and higher temperature curing air or other gas prior to being taken up on a winder or otherwise being processed or stored for eventual incorporation in membrane modules suitable for use in the desired separation operation. For the coating of polysulfone hollow fibers with the sulfonated polysulfone, which is a preferred embodiment of the present invention, it is generally desirable to employ drying temperatures of from about 50° C. to about 130° C. Those skilled in the art will appreciate that it is also possible to dry the separation layer on the support layer without employing the separate curing step noted above.

If desired, the support layer may be modified by a high temperature annealing process. Although it is preferable to anneal the substrate prior to its being coated with the separation layer, the annealing process may be carried out on the coated substrate as well. The resulting composite membrane formed from such an annealed substrate may provide increased resistance to pressure.

In use, the composite membrane will generally be assembled as part of a membrane separating device. The membrane device is designed to carry out a selective separation of at least one component from a fluid stream mixture. The membrane apparatus will typically consist of an enclosure and a membrane assembly positioned therein. The membrane assembly can be constructed in the form of a spiral wound cartridge, a hollow fiber bundle, a pleated flat sheet membrane assembly, and like assemblies common in the membrane industry. The membrane assembly is constructed so as to have a feed-surface side and an opposite permeate exit side. The enclosure is constructed so as to enable the feed stream mixture to be brought into contact with the membrane feed-surface side. Conduit means are provided for the removal of the part of the feed stream that did not permeate through the membrane, and for the separate removal of the permeate components that have passed through the membrane.

Reverse osmosis is the means by which the liquid separation of the present invention is carried out. In conducting the liquid separations, including concentrations, of the present invention, the exit side of the membrane is maintained at a pressure which is less than the pressure at the feed side. The driving force for the desired permeation through the membrane is a differential in the pressure drop across the membrane. Permeating components pass into and through the membrane and can be removed from the vicinity of the exit side of the membrane to maintain the desired driving force for the permeation. The functionality of the membrane does not depend upon the direction of feed flow or the surface of the membrane which is first contacted by the liquid feed medium.

The liquid feed medium sent to the membrane separator, e.g., an aqueous purge stream from the stripper bottoms, can be supplied to the membrane separator at a pressure in the range of from about 10 to about 1200 psig, preferably in the range of from about 50 to about 1000 psig, and most preferably in the range of from about 200 to about 1000 psig. The permeate pressure is generally maintained at a pressure which is about 30 psig to about 1000 psig less than that of the feed pressure.

The temperature of the liquid medium introduced to the separator can vary from below ambient to about 100° C., generally about 15° to about 80° C., and preferably about 20° to about 70° C.

The concentration of the impurities in the processing streams such as the UV absorbers and/or their precursors, e.g., the organic acids or their salts, and the like, is typically quite low. Thus, the concentration of the UV absorbers may vary from as low as 0% by weight to as much as 2.0% by weight, generally about 0.001% to about 0.1% by weight. The amount of ethylene glycols present in the liquid medium may vary over a wide range. Typically, the concentration of the glycols may be as low as 0% to as high as about 80.0% by weight, generally about 0.5% to about 10% by weight.

Figure 1:
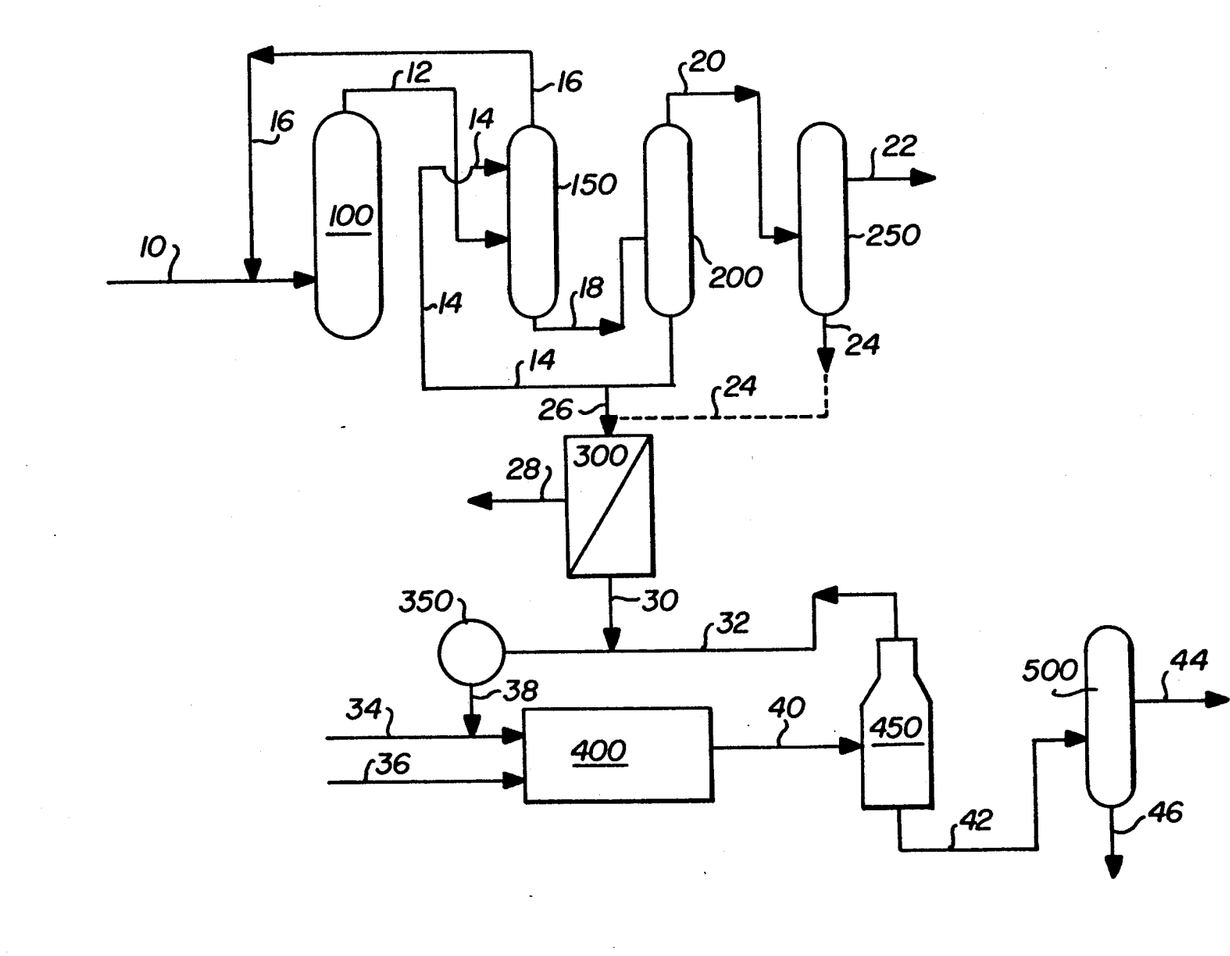
The Figure is a schematic diagram of a combined ethylene oxide/ethylene glycol manufacturing process utilizing a membrane separator in accordance with the present invention to separate UV absorber impurities from the stripper bottoms purge stream.

In the Figure, a schematic diagram is set forth showing how the present invention can be effectively utilized in the processes for the manufacture of ethylene oxide and polyester-grade ethylene glycol. It is to be understood that the following description is illustrative of only one embodiment of the conventional process for the production of ethylene oxide and/or ethylene glycol. Many variations and alternative embodiments exist for these processes which are well within the knowledge of those skilled in this art. Inasmuch as the present invention is specifically directed to the separation of UV absorbers, UV absorber precursors, and/or other impurity components, such as weak organic acids or their salts, from ethylene glycols, it will be appreciated that the present invention is not limited to only the embodiment discussed hereinafter. Rather, it is applicable to being used in any variation of the processes for the production of ethylene oxide/ethylene glycol, and indeed, is applicable to being used in any prooccessing environment where there is a need to separate constituents such as UV absorbers, UV absorber precursors, and/or other impurity components from ethylene glycols.

In particular, air or oxygen and ethylene are fed via line 10 to reactor 100 which is filled with a silver catalyst. The ethylene and oxygen react in the presence of the catalyst at a temperature typically in the range of from about 100° C. to about 500° C., and preferably in the range of from about 200° C. to 360° C. Although the principal product desired is ethylene oxide, the product stream leaving reactor 100 via line 12 also contains by-products of the oxidation reaction including water, and $CO_2$ as well as unreacted ethylene and a diluent gas such as nitrogen or methane. This overhead product stream containing the ethylene oxide is then introduced to scrubber 150 where it is countercurrently contacted with water entering the scrubber at line 14. The overhead from scrubber 150 is comprised principally of unreacted ethylene and the diluent gas and is recycled back to reactor 100 via line 16. The scrubber bottoms leaving the scrubber at line 18 principally contains ethylene oxide dissolved in water, i.e., an ethylene oxide-water stream, but typically also includes ethylene glycols and UV absorbers, UV absorber precursors, and/or other impurity components. Ethylene glycols are formed in the scrubber by the reaction of ethylene oxide and water.

The absorber bottoms in line 18 comprising the ethylene oxide-water stream is then introduced to stripper 200. In one alternative, steam (not shown) may be passed through the stripper in order to remove ethylene oxide which exits the stripper via line 20. In another alternative, steam is not introduced, but rather, the stripper is maintained at temperature and pressure conditions which are suitable for removing the ethylene oxide from the ethylene oxide-water stream as overhead.

The ethylene oxide leaving stripper 200 via line 20 is then fed to one or a series of purifying columns shown as column 250 in the drawing in which the ethylene oxide is purified by conventional techniques such as distillation, and the like, in which extraneous materials such as water, carbon dioxide, glycols, etc. are removed so as to produce essentially pure ethylene oxide in stream 22. The bottoms leaving purifying column 250 at line 24 may typically contain water, ethylene glycols and impurity components.

The aqueous bottoms stream leaving stripper 200 via line 14 principally comprises water and mono-, di-, and/or triethylene glycols and may also contain higher molecular weight glycols as well. Also included in this stream are the UV absorbers and/or their precursors as well as other impurity components. This stream is recycled back to scrubber 150 to provide the necessary scrubbing water.

In order to reduce the build-up of water in the recycle loop, however, a purge stream 26 must generally be provided. In the prior art, such a purge stream might simply be discarded and any glycols contained therein would simply be lost. Alternatively, if the glycols were to be salvaged, the UV absorbers, UV absorber precursors, and/or other impurity components typically contained in this purge stream would deleteriously affect the monoethylene glycol produced using this purge stream in the glycol process. In the present invention, however, such loss of the glycols is avoided while the undesirable UV absorbers, UV absorber precursors, and/or other impurity components are removed by passing the purge stream containing these impurities into a semi-permeable membrane separator 300.

Separator 300 is provided with a suitable semi-permeable membrane, preferably, a composite membrane comprising a sulfonated polysulfone coating on a polysulfone substrate. The permeate, which is that material passing through the membrane, has a much lower concentration of the impurity components, the UV absorbers and/or their precursors as compared to the raffinate, which is that material which does not pass through the membrane. In other words, the membrane separator is capable of allowing substantially most of the glycols to pass through the membrane while rejecting or preventing the UV absorbers, UV absorber precursors, and/or other impurity components from doing so. This provides a permeate which is essentially free of the undesirable UV absorbers, UV absorber precursors, and/or other impurity components and which primarily contains water and the glycols. The feed pressure provided to membrane separator 300 is between about 10 to about 1200 psig. preferably between about 50 to about 1000 psig. Permeate pressure is from about 0 psig to about 1170 psig, preferably about 0 to about 200 psig, but should be lower than the feed pressure by at least 30 psi, preferably at least 200 psi. The temperature of the feed to the membrane separator is typically in the range of from about 0° to about 100° C., preferably about 15° C. to about 80° C.

It is to be understood that although the drawing depicts the use of only one membrane separator, the scope of the present invention includes the embodiment in which more than one separator or "stage" is utilized. This would depend on the desired degree of recovery of the ethylene glycols.

The permeate is then passed out of the separator via line 30. The raffinate, which now contains a concentrated amount of UV absorbers, UV absorber precursors, and/or other impurity components, is passed out of the separator via line 28. This raffinate may be discarded or further processed in another stage (not shown) as may be desired.

If desired, bottoms stream 24 from purifying column 250 which may contain water and glycols, may also be introduced to separator 300 as shown by the dotted line so as to recover the glycols contained therein. Indeed, any impurity-containing glycol/water stream found anywhere within an ethylene oxide or ethylene glycol process may be purified in such a manner.

The permeate from line 30 may then be utilized in the manufacturing process for the preparation of polyester-grade monoethylene glycol. In particular, it may be added to water recycle stream 32 and introduced to water tank 350. Water from tank 350 is passed via line 38 to glycol reactor 400. Additional water, if desired, may also be introduced to reactor 400 via line 34. Line 36 supplies ethylene oxide whose source will typically be from purifying column 250 in the ethylene oxide production process. In the glycol reactor, the ethylene oxide and water react at a temperature typically in the range of from about 150° C. to about 310° C. at a pressure of from about 100 to about 300 psig. The resultant mixture comprising ethylene glycols in water is then passed via line 40 to one or more evaporators shown in the drawing as evaporator 450. As an alternative embodiment, the permeate from separator 300 may be introduced directly into evaporator 450 (not shown) via lines 30 and 40. If desired, a multi-effect evaporator may be utilized. In the evaporator(s), steam is produced as overhead, is condensed (not shown), and is recycled via line 32 to the water tank 350 and then on to reactor 400. The ethylene glycols bottoms leaving the evaporator at line 42 is then subjected to a number of distillation steps which is shown as column 500 in the drawing, to separate the desired polyester-grade monoethylene glycol in stream 44 from the remaining glycols which is shown in the diagram as being removed from line 46.

The invention is hereafter further described with respect to various illustrative examples thereof. It should be understood, however, that such examples should not be construed as limiting the scope of the invention which is set forth in the appended claims.

EXAMPLES

In the following examples, the units used to describe the results obtained are defined as follows.

"Stage Cut" is a measure of how much feed the separator module can treat. It is defined as the ratio of permeate flowrate to the feed flowrate. The higher the stage cut, the higher the glycol recovery and the higher the concentration of impurities in the raffinate.

"gfd" is a measure of the flowrate of the permeate through the membrane and stands for gallon/square foot/day.

"% Solute Rejection" is a measure of how much of a particular solute is rejected by the membrane such that it remains in the raffinate. As used herein, it is defined as:

(Conc. of solute in feed - Conc. of solute in permeate) * 100/(Conc. of solute in feed) Except where indicated, the concentration of the salts in either the feed or permeate is measured in terms of its electrical conductivity (micro mho).

Ideally, the reverse osmosis separation should combine a high solute rejection with a large permeation rate for a large stage cut. Under such conditions, the membrane separator would produce a large flux of UV absorber-free glycol solution and a relatively small raffinate stream rich in impurities.

For the test results shown in the following tables, the particular membranes utilized are described therein. Conductivity measurements were made with a platinum cell, particularly a Cole Parmer digital conductivity meter. UV transmittance was measured using a Varian model DMS 100 UV-Visible Spectrophotometer.

Moreover, UV transmittance data was carried out on a sample which was made by first mixing a permeate stream prepared in accordance with the present invention with a portion of an ethylene glycols bottoms stream leaving an evaporator in an ethylene glycol process (stream 42 in the Figure). This mixture is then distilled to remove water and the ethylene glycol refined. It is this ethylene glycol sample which was then tested for its UV transmittance.

TABLE I

|  | Untreated Feed | Permeate* | Distilled Water |
|---|---|---|---|
| Solute Comp. |  |  |  |
| Formate (ppm) | 25.8 | 17.2 | 0 |
| Acetate (ppm) | 17.1 | 2.8 | 0 |
| Glycolate (ppm) | 54.0 | 6.7 | 0 |
| UV, % Transmittance |  |  |  |
| 220 nm | 76.9 | 77.0 | 81.0 |
| 275 nm | 89.0 | 95.7 | 97.1 |
| 350 nm | 100.6 | 101.4 | 100.9 |

*The permeate was obtained using a composite membrane having a coating of sulfonated polysulfone with a degree of sulfonation of 1.8 meq/gm of sulfonic acid groups in the polymer on a polysulfone substrate comprised of hollow fibers. The fibers have a 14 mil OD and a 5 mil ID.

As can readily be seen from the above table, passing the feed stream through a semi-permeable membrane dramatically improves the UV transmittance of the refined monoethylene glycol with respect to all of the wavelengths that were tested. Indeed, the UV transmittance of the refined monoethylene glycol actually approached that of a refined glycol stream prepared with distilled water instead of the permeate.

TABLE II a

| | | Solute Rejection Characteristics | | | | | |
|---|---|---|---|---|---|---|---|
| Experiment No. | Feed Pressure | Permeate Flowrate | Stage Cut | MEG* Rejection | Acetate Rejection | Formate Rejection | Glycolate Rejection |
| 1 | 220 psi | 7.2 l/hr | 0.34 | 36.6 | 84.3 | 93.9 | 94.1 |
| 2 | 220 | 7.5 | 0.36 | 21.2 | 87.6 | 95.6 | 96.3 |
| 3 | 380 | 11.1 | 0.74 | 12.8 | 84.0 | 84.3 | 89.1 |
| 4 | 380 | 11.4 | 0.76 | 13.1 | 85.0 | 86.7 | 92.0 |

*MEG = monoethylene glycol
All "Rejection" data is given as percent.

TABLE II b

| Experiment No. | Feed Pressure | MEG* (%) | Acetate (ppm) | Formate (ppm) | Glycolate (ppm) |
|---|---|---|---|---|---|
| FEED COMPOSITION |  | 1.74 | 22.31 | 107.92 | 35.22 |
| 1 | 220 psi |  |  |  |  |
| Permeate |  | 1.37 | 3.49 | 6.58 | 2.08 |
| Raffinate |  | 1.88 | 39.67 | 264.24 | 57.69 |
| 2 | 220 psi |  |  |  |  |
| Permeate |  | 1.37 | 2.76 | 4.74 | 1.31 |
| Raffinate |  | 1.85 | 37.53 | 222.33 | 47.53 |
| 3 | 380 psi |  |  |  |  |
| Permeate |  | 1.52 | 3.57 | 16.98 | 3.59 |
| Raffinate |  | 2.46 | 85.17 | 831.71 | 175.74 |
| 4 | 380 psi |  |  |  |  |
| Permeate |  | 1.50 | 3.35 | 14.31 | 2.82 |
| Raffinate |  | 2.32 | 96.83 | 691.05 | 146.64 |

The membranes used for Examples 1 through 4 were the same as that used in Table I with the exception that the hollow fibers had an OD of 15.5 mils and an ID of 5.5 mils.
*MEG = monoethylene glycol

TABLE III

| Experiment No. | Temp. (°C.) | Feed Press. (psi) | Feed Flowrate (l/hr) | Permeate Flowrate (l/hr) | Permeate Flowrate (gfd) | Stage Cut (%) | Permeate Conduct. (mi · mho) | Salt Rejection (%) | MEG* Rejection (%) | UV Trans. 275 nm (%) | Membrane No. |
|---|---|---|---|---|---|---|---|---|---|---|---|
| 5 | 25 | 860 | 39 | 21.0 | 3.2 | 53.8 | 17.1 | 94.4 | 32.5 |  | 1 |
| 6 | 25 | 860 | 38.4 | 21.0 | 3.2 | 54.7 | 20.1 | 93.0 | 37.8 |  | 1 |
| 7 | 25 | 860 | 38.4 | 20.4 | 3.1 | 53.1 | 14.1 | 95.0 | 37.8 |  | 1 |
| 8 | 25 | 860 | 36.0 | 20.4 | 3.1 | 56.7 | 14.8 | 94.3 | 31.0 |  | 1 |
| 9 | 40 | 860 | 35.7 | 27.9 | 4.3 | 78.2 | 34.7 | 85.0 | 15.0 |  | 1 |
| 10 | 40 | 860 | 35.4 | 29.4 | 4.5 | 83.1 | 51.3 | 77.0 | 5.3 |  | 1 |
| 11 | 40 | 860 | 51.6 | 30.0 | 4.6 | 58.1 | 32.0 | 86.8 | 20.2 |  | 1 |
| 12 | 40 | 860 | 51.0 | 30.0 | 4.6 | 58.8 | 30.8 | 88.4 | 22.4 |  | 1 |
| 13 | 35 | 600 | 36.5 | 28.8 | 4.4 | 78.9 | 35.0 | 88.9 | 9.1 |  | 2 |
| 14 | 35 | 750 | 54.9 | 36.0 | 5.5 | 65.6 | 27.0 | 90.9 | 11.7 |  | 2 |
| 15 | 35 | 750 | 55.5 | 36.0 | 5.5 | 64.9 | 28.0 | 91.0 | 15.2 | 95.3 | 2 |
| 16 | 35 | 750 | 54.0 | 36.0 | 5.5 | 66.7 | 33.0 | 88.7 | 15.2 |  | 2 |
| 17 | 25 | 600 | 36.8 | 23.2 | 3.5 | 63.0 | 42.0 | 90.3 |  |  | 2 |
| 18 | 25 | 500 | 37.0 | 18.0 | 2.7 | 48.6 | 22.0 | 91.3 |  |  | 2 |
| 19 | 35 | 500 | 61.9 | 24.0 | 3.7 | 38.8 | 21.0 | 92.1 | 22.1 |  | 2 |
| 20 | 45 | 500 | 58.8 | 30.0 | 4.6 | 51.0 | 38.0 | 85.4 |  |  | 2 |
| 21 | 54 | 500 | 60.0 | 40.0 | 6.1 | 66.7 | 66.0 | 72.0 |  |  | 2 |
| 22 | 25 | 500 | 59.8 | 17.5 | 2.7 | 29.3 | 33.0 | 88.0 | 21.9 |  | 2 |

TABLE III-continued

| Experiment No. | Temp. (°C.) | Feed Press. (psi) | Feed Flowrate (1/hr) | Permeate Flowrate (1/hr) | Permeate Flowrate (gfd) | Stage Cut (%) | Permeate Conduct. (mi · mho) | Salt Rejection (%) | MEG* Rejection (%) | UV Trans. 275 nm (%) | Membrane No. |
|---|---|---|---|---|---|---|---|---|---|---|---|
| 23 | 35 | 500 | 61.1 | 23.2 | 3.5 | 38.0 | 39.0 | 84.8 | 20.3 | 94.2 | 2 |
| 24 | 45 | 500 | 54.2 | 31.0 | 4.7 | 57.2 | 50.0 | 78.5 | 11.1 | | 2 |
| 25 | 55 | 500 | 58.9 | 40.0 | 6.1 | 67.9 | 78.0 | 65.9 | 5.0 | | 2 |
| 26 | 25 | 700 | 69.8 | 24.8 | 7.1 | 35.5 | 9.0 | 97.6 | | | 3 |
| 27 | 35 | 700 | 67.9 | 30.0 | 8.6 | 44.2 | 11.0 | 97.1 | 38.9 | | 3 |
| 28 | 45 | 700 | 70.3 | 36.0 | 10.4 | 51.2 | 35.0 | 89.2 | 29.5 | 93.6 | 3 |
| 29 | 55 | 700 | 66.7 | 45.0 | 13.0 | 67.5 | 51.0 | 87.2 | 22.9 | | 3 |
| 30 | 45 | 900 | 66.4 | 42.2 | 12.2 | 63.6 | 44.0 | 85.9 | 26.3 | | 3 |
| 31 | 25 | 800 | 38.0 | 18.0 | 5.2 | 47.4 | 8.0 | 95.9 | 35.1 | 94.3 | 3 |
| 32 | 25 | 600 | 37.5 | 18.5 | 5.1 | 49.3 | 6.6 | 97.2 | | | 4 |
| 33 | 25 | 700 | 32.0 | 20.0 | 5.5 | 62.5 | 6.8 | 96.6 | | | 4 |
| 34 | 49 | 600 | 65.7 | 32.7 | 9.0 | 49.8 | 12.9 | 93.5 | 21.1 | 92.5 | 4 |
| 35 | 50 | 600 | 43.0 | 30.0 | 8.2 | 69.8 | 18.0 | 92.9 | | | 4 |
| 36 | 50 | 950 | 71.2 | 42.4 | 11.6 | 59.6 | 15.0 | 93.7 | | | 4 |
| 37 | 50 | 600 | 69.8 | 30.0 | 8.2 | 43.0 | 18.0 | 92.9 | | 98.3 | 4 |

*MEG = monoethylene glycol

The membrane modules 1-4 utilized in the experiments of Table III were substantially the same as those used in the previous experiments with the exception that there was a variation in the drying and/or curing time of the polymers comprising the coating of the membrane. This slightly affects the separation and permeation characteristics. In particular, the rejection generally increases and the flux generally decreases as the drying and/or curing temperature is increased. So too, membrane module nos. 1 and 2 were made with hollow fibers having an OD of 10 mils and an ID of 3.5 mils. Membrane module nos. 3 and 4 were made with hollow fibers having an OD of 16 mils and an ID of 5 mils. All of the membranes were helically wound, coated fiber membrane modules made as described in U.S. Pat. No. 4,207,192.

Table III shows the effects of temperature, pressure and flow rate on the membrane separator. As shown by the results in the Table, temperature affects the permeation and the rejection. It is believed that this is caused by the effect that the temperature has on the viscosity of the liquid medium. Higher temperatures decrease the vicosity and as a result, the permeation rate increases with temperature and the rejection decreases.

As to pressure, the Table shows that higher pressures produce higher permeation rates. For large stage cuts, this decreases the solute rejection.

Moreover, as the feed flowrate increases, the velocity of the liquid at the surface of the membrane increases. This decreases the thickness of the layer of salt which tends to accumulate at the membrane surface. In this layer, called the polarization layer, the concentration of salt is higher than in the feed solution. For higher feed flowrates, the polarization diminishes and the concentration of salt at the membrane surface decreases. This improves the rejection of the salts inasmuch as the salt concentration gradient across the membrane is less.

What is claimed is:

1. A method for separating ethylene glycols from at least one impurity component comprising an aliphatic organic acid having one or more carbon atoms, an alkali metal or alkaline earth metal salt of such aliphatic organic acid, or a combination thereof; said glycols and said at least one impurity component being substantially dissolved in a liquid medium capable of acting as a solvent for said glycols and the at least one impurity, which comprises contacting the liquid medium containing said glycols and the at least one impurity with one surface of a semi-permeable membrane which exhibits selective permeation of the glycols over that of the at least one impurity, the semi-permeable membrane being an asymmetric membrane or a composite membrane, and removing from the vicinity of the opposite surface of the semi-permeable membrane a permeate having a concentration of the at least one impurity which is less than the concentration of the at least one impurity in the liquid medium and having properties suitable for the preparation of substantially polyester grade glycols.

2. The method of claim 1, wherein the ethylene glycols comprise mono-, di-, tri- and/or tetraethylene glycol.

3. The method of claim 1, wherein the membrane is a composite membrane comprising a porous support layer having substantially no separation characteristics with respect to the liquid medium and a separation layer positioned on the support layer which substantially determines the selective permeation characteristics of the composite membrane.

4. The method of claim 3, wherein the support layer comprises at least one of polysulfone, polyolefins, polyphenylenesulfide and polyether ketone.

5. The method of claim 3, wherein the support layer is polysulfone.

6. The method of claim 3, wherein the separation layer comprises at least one of sulfonated polysulfone, cellulosic polymers, cellulose acetate, polyamides, and mixtures thereof.

7. The method of claim 3, wherein the separation layer is a sulfonated polysulfone.

8. The method of claim 8, wherein the sulfonated polysulfone is sulfonated bisphenol A polysulfone.

9. The method of claim 3, wherein the separation layer has a thickness in the range of from about 0.01 to 10.0 microns.

10. The method of claim 3, wherein the separation layer has a thickness in the range of from about 0.05 to 2.0 microns.

11. The method of claim 3, wherein the separation layer comprises sulfonated polysulfone and the support layer comprises polysulfone.

12. The method of claim 3, wherein the separation layer is comprised of cellulose acetate and the support layer is comprised of polysulfone.

13. The method of claim 3, wherein the support layer is an annealed polymeric material.

14. The method of claim 1, wherein the composite membrane is in hollow fiber form.

15. The method of claim 1, wherein the membrane is an asymmetric membrane comprising at least one of sulfonated polysulfone, cellulosic polymers, cellulose acetate, polyamides, and mixtures thereof.

16. The method of claim 1, wherein the membrane is an asymmetric membrane comprising sulfonated polysulfone.

17. The method of claim 16, wherein the sulfonated polysulfone is sulfonated bisphenol A polysulfone.

18. The method of claim 1, wherein the at least one aliphatic organic acid is formic acid, acetic acid, glycolic acid, oxalic acid, or combinations thereof.

19. The method of claim 1, wherein the at least one salt comprises an alkali metal or alkaline earth metal salt of formic acid, acetic acid, glycolic acid and/or oxalic acid.

20. The method of claim 1, wherein the liquid medium in which said glycol and the at least one salt and/or acid are contained is selected from the group consisting of water, alcohols, glycols, glycol ethers, glycol carbonates, or mixtures thereof.

21. The method of claim 1, wherein the liquid medium in which said glycol and the least one salt and/or acid are contained is water.

22. A method of separating ethylene glycols from at least one UV absorber and/or UV absorber precursor; said glycols and said at least one UV absorber and/or UV absorber precursor being substantially dissolved in a liquid medium capable of acting as a solvent for said glycols and the at least one UV absorber and/or precursor, which comprises contacting the liquid medium containing said glycols and the at least one UV absorber and/or precursor with one surface of a semi-permeable membrane which exhibits selective permeation for the glycols over that of the at least one UV absorber and/or precursor, the semi-permeable membrane being an asymmetric membrane or a composite membrane, and removing from the vicinity of the opposite surface of the semi-permeable membrane a permeate having a concentration of the UV absorber and/or precursor which is less than the concentration of the UV absorber and/or precursor in the liquid medium and having properties suitable for the preparation of substantially polyester grade glycols.

23. The method of claim 22, wherein the ethylene glycols comprise mono-, di-, tri and/or tetraethylene glycol.

24. The method of claim 22, wherein the membrane is a composite membrane comprising a porous support layer having substantially no separation characteristics with respect to the aqueous medium and a separation layer positioned on the support layer to substantially determine the selective permeation characteristics of the composite membrane.

25. The method of claim 24, wherein the separation layer is a sulfonated polysulfone.

26. The method of claim 25, wherein the sulfonated polysulfone is sulfonated bisphenol A polysulfone.

27. The method of claim 24, wherein the separation layer has a thickness in the range of from about 0.01 to 10.0 microns.

28. The method of claim 24, wherein the separation layer has a thickness in the range of from about 0.05 to 2.0 microns.

29. The method of claim 24, wherein the separation layer is a sulfonated polysulfone and the support layer is a polysulfone.

30. The method of claim 24, wherein the separation layer is comprised of cellulose acetate and the support layer is comprised of polysulfone.

31. The method of claim 24, wherein the support layer is an annealed polymeric material.

32. The method of claim 24, wherein the support layer comprises at least one of polysulfone, polyolefins, polyphenylenesulfide and polyether ketone.

33. The method of claim 24, wherein the support layer is polysulfone.

34. The method of claim 24, wherein the separation layer comprises at least one of sulfonated polysulfone, cellulosic polymers, cellulose acetate, polyamides, and mixtures thereof.

35. The method of claim 22, wherein the composite membrane is in hollow fiber form.

36. The method of claim 22, wherein the membrane is an asymmetric membrane comprising at least one of sulfonated polysulfone, cellulosic polymers, cellulose acetate, polyamides, and mixtures thereof.

37. The method of claim 22, wherein the membrane is an asymmetric membrane comprising a sulfonated polysulfone.

38. The method of claim 37, wherein the sulfonated polysulfone is sulfonated bisphenol A polysulfone.

39. The method of claim 22, wherein the UV absorbers and/or UV absorber precursors are one or more of an aliphatic organic acid having one or more carbon atoms, an alkali metal or alkaline earth metal salt of such aliphatic organic acid, or a combination thereof.

40. The method of claim 39, wherein the at least one aliphatic organic acid is formic acid, acetic acid, glycolic acid, oxalic acid, or combinations thereof.

41. The method of claim 39, wherein the at least one salt comprises an alkali metal or alkaline earth metal salt of formic acid, acetic acid, glycolic acid and/or oxalic acid.

42. The method of claim 22, wherein the liquid medium in which said glycol and the at least one UV absorber and/or precursors are contained is selected from the group consisting of water, alcohols, glycols, glycol ethers, glycol carbonates, or mixtures thereof.

43. The method of claim 22, wherein the liquid medium in which said glycol and the at least one UV absorber and/or precursor are contained is water.

44. In a process for the manufacture of ethylene oxide which includes the steps of:
a) reacting oxygen and ethylene in a reactor in the presence of a catalyst at ethylene oxide producing conditions to produce ethylene oxide;
b) absorbing ethylene oxide produced in step (a) in water in a scrubber to produce an ethylene oxide-water stream;
c) stripping ethylene oxide from the ethylene oxide-water stream produced in step (b) in a stripping column to produce an ethylene oxide overhead stream and an aqueous bottoms stream, said aqueous bottoms stream comprising water, UV absorbers and/or UV absorber precursors, and mono-,di-, and/or triethylene glycol;
d) recycling aqueous bottoms from the stripping column to the scrubber of step (b); the improvement which comprises removing as a purge stream a portion of the recycled aqueous bottoms from the stripping column of step (c) and treating at least a portion of said purge stream by contacting the purge stream containing the glycol and at least one UV absorber and/or UV absorber precursor with one surface of a semi-permeable membrane which exhibits selective permeation for the glycol over that of the at least one UV absorber and/or UV absorber precursor, the semi-permeable membrane being an asymmetric membrane or a composite membrane, and removing from the vicinity of the opposite surface of the semi-permeable membrane a permeate having a concentration of the UV absorber and/or UV absorber precursor which is less than the concentration of the UV absorber and/or UV absorber precursor in the purge stream and having properties suitable for the preparation of substantially polyester grade glycols.

45. The process of claim 44, wherein the membrane is a composite membrane comprising a porous support layer having substantially no separation characteristics with respect to the purge stream and a separation layer positioned on the support layer to substantially determine the selective permeation characteristics of the composite membrane.

46. The process of claim 45, wherein the separation layer has a thickness in the range of from about 0.01 to 10.0 microns.

47. The process of claim 45, wherein the separation layer has a thickness in the range of from about 0.05 to 2.0 microns.

48. The process of claim 45, wherein the separation layer comprises sulfonated polysulfone and the support layer comprises polysulfone.

49. The process of claim 45, wherein the separation layer is comprised of cellulose acetate and the support layer is comprised of polysulfone.

50. The process of claim 45, wherein the support layer is an annealed polymeric material.

51. The process of claim 44, wherein the semi-permeable membrane is in hollow fiber form.

52. The process of claim 45, wherein the support layer comprises at least one polysulfone, polyolefins, polyphenylenesulfide and polyether keytone.

53. The process of claim 45, wherein the support layer is polysulfone.

54. The process of claim 45, wherein the separation layer comprises at least one of sulfonated polysulfone, cellulosic polymers, cellulose acetate, polyamides, and mixtures thereof.

55. The process of claim 45, wherein the separation layer is a sulfonated polysulfone.

56. The process of claim 55, wherein the sulfonated polysulfone is sulfonated bisphenol A polysulfone.

57. The process of claim 45, wherein the separation layer is a sulfonated polysulfone and the support layer is a polysulfone.

58. The process of claim 44, wherein the membrane is an asymmetric membrane comprising at least one of sulfonated polysulfone, cellulosic polymers, cellulose acetate, polyamides, and mixtures thereof.

59. The process of claim 44, wherein the membrane is an asymmetric membrane comprising a sulfonated polysulfone.

60. The process of claim 59, wherein the sulfonated polysulfone is sulfonated bisphenol A polysulfone.

61. The process of claim 44, wherein the permeate is fed to an ethylene glycol reactor or an evaporator train.

62. The process of claim 44, wherein the UV absorber and/or UV absorber precursor are one or more of an aliphatic organic acid having one or more carbon atoms, an alkali metal or alkaline earth metal salt of such aliphatic organic acid, or a combination thereof.

63. In a process for the manufacture of ethylene oxide and ethylene glycol which includes the steps of:
   a) reacting oxygen and ethylene in a reactor in the presence of a catalyst at ethylene oxide producing conditions to produce ethylene oxide;
   b) absorbing ethylene oxide produced in step (a) in water in a scrubber to produce an ethylene oxide-water stream;
   c) stripping ethylene oxide from the ethylene oxide-water stream produced in step (b) in a stripping column to produce an ethylene oxide overhead stream and an aqueous bottoms stream, said aqueous bottoms stream comprising water, UV absorbers and/or UV absorber precursors, and mono-, di-, and/or triethylene glycol;
   d) recycling aqueous bottoms from the stripping column to the scrubber of step (b);
   e) purifying the ethylene oxide overhead stream from the stripping column of step (c) by distillation to provide a purified ethylene oxide stream, at least a portion of which is introduced to a glycol reactor;
   f) reacting ethylene oxide and water in the glycol reactor to produce a product stream comprising ethylene glycols in water;
   g) evaporating water from the product stream produced in step (f) in an evaporator to produce a glycols product stream; and recycling evaporated water to the glycol reactor;
   h) removing as a purge stream a portion of the recycled aqueous bottoms from the stripping column of step (c) and introducing the purge stream to said glycol reactor and/or evaporator; and
   i) distilling the glycols product stream produced in step (g) to produce a monoethylene glycol product; the improvement which comprises treating the purge stream of the recycled aqueous bottoms from the stripping column of step (c) prior to its being introduced to the glycol reactor and/or evaporator by contacting the purge stream which contains mono-, di-, and/or triethylene glycols and at least one UV absorber and/or UV absorber precursor with one surface of a semi-permeable membrane which exhibits selective permeation for the glycols over that of the at least one UV absorber and/or UV absorber precursor, the semi-permeable membrane being an asymmetric membrane or a composite membrane, and removing from the vicinity of the opposite surface of the semi-permeable membrane a permeate having a concentration of the UV absorber and/or UV absorber precursor which is less than the concentration of the UV absorber and/or UV absorber precursor in the purge stream and having properties suitable for the preparation of substantially polyester grade glycols.

64. The method of claim 63, wherein the UV absorbers and/or UV absorber precursors are one or more of an aliphatic organic acid having one or more carbon atoms, an alkali metal or alkaline earth metal salt of such aliphatic organic acid, or a combination thereof.

65. The process of claim 63, wherein the membrane is a composite membrane comprising a porous support layer having substantially no separation characteristics with respect to the purge stream and a separation layer positioned on the support layer which substantially determines the selective permeation characteristics of the composite membrane.

66. The process of claim 65, wherein the support layer comprises at least one of polysulfone, polyolefins, polyphenylenesulfide and polyether ketone.

67. The process of claim 65, wherein the support layer is polysulfone.

68. The process of claim 65, wherein the separation layer comprises at least one of sulfonated polysulfone, cellulosic polymers, cellulose acetate, polyamides, and mixtures thereof.

69. The process of claim 65, wherein the separation layer is a sulfonated polysulfone.

70. The process of claim 69, wherein the sulfonated polysulfone is sulfonated bisphenol A polysulfone.

71. The process of claim 65, wherein the separation layer comprises sulfonated polysulfone and the support layer comprises polysulfone.

72. The process of claim 65, wherein the separation layer is comprised of cellulose acetate and the support layer is comprised of polysulfone.

73. The process of claim 65, wherein the support layer is an annealed polymeric material.

74. The process of claim 63, wherein the semi-permeable membrane is in hollow fiber form.

75. The process of claim 63, wherein the membrane is an asymmetric membrane comprising at least one of sulfonated-polysulfone, cellulosic polymers, cellulose acetate, polyamides, and mixtures thereof.

76. The process of claim 63, wherein the membrane is an asymmetric membrane comprising a sulfonated polysulfone.

77. The process of claim 76, wherein the sulfonated polysulfone is sulfonated bisphenol A polysulfone.

* * * * *

UNITED STATES PATENT AND TRADEMARK OFFICE
CERTIFICATE OF CORRECTION

PATENT NO. : 5,034,134
DATED : July 23, 1991
INVENTOR(S) : K.F. George et al.

It is certified that error appears in the above-identified patent and that said Letters Patent is hereby corrected as shown below:

Column 4, line 10, after "from" insert --the vicinity of--

Column 9, line 53, "Sulfonated Polysulfone" should be underlined.

Column 10, line 16, "Particularly" should read --particularly-- line 21, "--$SO_3^{31}$" should read -- --$SO_3^-$--

Column 15, line 34, under "TABLE 1" insert --UV Transmittance Comparison--.

Claim 8, line 1, "8" should be --7--

Signed and Sealed this

Fifth Day of January, 1993

*Attest:*

DOUGLAS B. COMER

*Attesting Officer*     *Acting Commissioner of Patents and Trademarks*